United States Patent [19]

Schrage et al.

[11] Patent Number: 5,315,049

[45] Date of Patent: May 24, 1994

[54] PROCESS FOR THE NUCLEAR CHLORINATION OF AROMATIC HYDROCARBONS

[75] Inventors: Heinrich Schrage, Krefeld; Helmut Fiege, Leverkusen, both of Fed. Rep. of Germany

[73] Assignee: Bayer Aktiengesellschaft, Leverkusen, Fed. Rep. of Germany

[21] Appl. No.: 108,367

[22] Filed: Aug. 18, 1993

[30] Foreign Application Priority Data

Aug. 25, 1992 [DE] Fed. Rep. of Germany ....... 4228134

[51] Int. Cl.$^5$ .................... C07C 17/12; C07C 25/00
[52] U.S. Cl. .................... 570/210; 570/206; 570/207; 570/208
[58] Field of Search ............... 570/206, 207, 210, 208

[56] References Cited

U.S. PATENT DOCUMENTS

| | | | |
|---|---|---|---|
| 3,000,975 | 9/1961 | De Bella | 570/206 |
| 3,226,447 | 12/1965 | Bing et al. | 570/206 |
| 4,166,075 | 8/1979 | Blumenfeld et al. | 570/210 |
| 4,186,153 | 1/1980 | Potts | 570/210 |
| 4,289,916 | 9/1981 | Nakayama et al. | 570/210 |

FOREIGN PATENT DOCUMENTS 0307934 3/1989 European Pat. Off. ............ 570/210

*Primary Examiner*—Werren B. Lone
*Attorney, Agent, or Firm*—Sprung Horn Kramer & Woods

[57] ABSTRACT

Alkylaromatics are subjected to nuclear chlorination in the liquid phase in the presence of Friedel-Crafts catalyst mixtures comprising compounds of iron and antimony and cocatalysts of the formula (II)

$$R_1-O-\left[CH_2-\underset{R_3}{\underset{|}{CH}}-O\right]_x-R_2 \quad (II)$$

wherein the substituents have the meaning given in the description.

9 Claims, No Drawings

PROCESS FOR THE NUCLEAR CHLORINATION OF AROMATIC HYDROCARBONS

The invention relates to an improved process for the nuclear chlorination of aromatic hydrocarbons in the presence of a mixture of Friedel-Crafts catalysts and in the presence of cocatalysts in the liquid phase.

The reaction of aromatic hydrocarbons in the liquid phase with gaseous chlorine to give nuclear-substituted chlorine derivatives is known (see Ullmanns Encyclopä die der technischen Chemie (Ullmann's Encyclopaedia of Industrial Chemistry), 4th edition, Volume 9, paqes 499 et seq.). This chlorination is in general carried out in the presence of Friedel-Crafts catalysts. A mixture of isomeric monochlorinated and polychlorinated compounds is obtained as the chlorination product. If $FeCl_3$ and sulphur are used as the catalyst and cocatalyst respectively, a mixture of monochlorotoluenes and dichlorotoluenes, for example, is obtained from toluene. The monochlorotoluene fraction contains the main products o-chlorotoluene and p-chlorotoluene, together with a small amount of m-chlorotoluene. The ratio of o-chlorotoluene to p-chlorotoluene is about 1.1:1.

Since all monochlorotoluenes are useful intermediate products, attempts have already been made to increase the selectivity of the formation of individual isomers. The catalyst used is of particular importance for the composition of the chlorination product, the known catalysts allowing a wide range. An overview is to be found in Ullmann's Encyclopaedia of Industrial Chemistry, 5th edition, Volume A6, page 343. $FeCl_3$, which, because of its high reactivity, already ensures almost complete conversion of chlorine at low concentrations, is often used as the catalyst on an industrial scale. However, a disadvantage is that relatively large amounts of more highly chlorinated products are formed. The product of the chlorination of toluene with $FeCl_3$ as the catalyst thus already contains 9% by weight of undesirable dichlorotoluenes at a chlorine conversion of 95 mol %.

The stage selectivity can be increased by addition of sulphur. At the same time, however, the ratio of o-chlorotoluene to p-chlorotoluene is reduced to 1.1:1.

The chlorination of toluene using titanium tetrachloride, tin tetrachloride, tungsten hexachloride and zirconium tetrachloride as catalysts is known from U.S. Pat. No. 3,000,975. The ratio of o-chlorotoluene to p-chlorotoluene which can be achieved is 3.3:1, and is therefore very high. However, the high catalyst concentration required, of about 1% by weight, based on toluene, which is about 50 times higher than the catalyst concentration required for $FeCl_3$ catalysis, is a disadvantage in this process. Another disadvantage is that a high content of o-chlorotoluene is achieved only if iron is excluded completely. For example, an addition of only 10 ppm of $FeCl_3$, a concentration which is rapidly reached under industrial conditions, leads to the same low ratio of o-chlorotoluene to p-chlorotoluene and the same poor stage selectivity as are obtained using pure $FeCl_3$ as the catalyst.

The chlorination of toluene with $SbCl_3$ is furthermore known from U.S. Pat. No. 3,226,447. The ratio of o-chlorotoluene to p-chlorotoluene observed with this catalyst is 1.6:1.

There is thus still a demand for an industrially usable catalytic system with which a good stage selectivity and a high content of o-chlorine compounds in the reaction mixture can be realised at the same time with small amounts of catalyst.

A process has now been found for the nuclear chlorination of aromatic hydrocarbons of the formula (I)

in which

R denotes a $C_1$-$C_{12}$-alkyl radical or $C_3$-$C_8$-cycloalkyl radical, in the presence of a mixture of Friedel-Crafts catalysts and in the presence of cocatalysts in the liquid phase, which is characterised in that the Friedel-Crafts catalysts employed are a mixture of at least one antimony and at least one iron compound and the cocatalyst employed is at least one compound having a polyether structure of the formula (II)

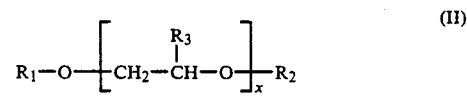

in which $R_1$ and $R_2$ independently of one another in each case represent hydrogen, a $C_1$-$C_{18}$-alkyl radical or $C_3$-$C_8$-cycloalkyl radical, or $R_1$ and $R_2$ together represent the radical of a cyclising alkylene group, $R_3$ denotes hydrogen, methyl or ethyl and x denotes a number from 1 to 500.

In a preferred embodiment of the process according to the invention, toluene, ethylbenzene, propylbenzene, cumene, tert-butylbenzene or phenylcyclohexane are employed as the aromatic hydrocarbons of the formula (I).

The process according to the invention is carried out in the liquid phase, that is to say the aromatic hydrocarbon of the formula (I) must be predominantly in the liquid form at reaction temperature. If appropriate, it can be employed together with an inert solvent. Suitable solvents are those which are not attacked by chlorine under nuclear chlorination conditions. For example, chlorinated aliphatic hydrocarbons, such as methylene chloride, chloroform and carbon tetrachloride, and acetic acid are suitable. Preferably, however, the reaction is carried out without addition of a solvent.

Elemental chlorine is preferably used as the chlorinating agent for the process according to the invention. This can be passed into the reaction mixture in liquid or gaseous form. Gaseous chlorine is preferably employed.

The nuclear chlorination to be carried out according to the invention can in principle be carried out at any desired temperatures between the solidification point and the boiling point of the reaction mixture. The reaction temperature is in general in the range between 0° and 100° C., preferably in the range between 20° and 80° C., especially preferably in the range from 40° to 60° C. The pressure can be normal, reduced or increased during the reaction, and in principle is not critical. Normal pressure is preferred because of the inexpensive procedure. Increased pressure may be indicated, for example, if the reaction is to be carried out in the presence of a solvent which is low-boiling under normal pressure. In this case, for example, the reaction can be carried out under the autogenous pressure established by the reaction mixture. The chlorination is preferably carried out such that the degree of chlorination in the reaction mixture, based on the aromatic hydrocarbon to be chlorinated, does not exceed 1. Higher degrees of chlorination are possible, but normally are not advantageous, because they lead to the formation of mostly undesirable polychlorinated products.

The chlorinating agent is therefore preferably employed in an amount of 0.8 to 1.1, preferably 0.8 to 1.0 mol per mole of the aromatic hydrocarbon.

The antimony compounds are preferably antimony halides, in particular antimony(III) chloride and antimony(V) chloride. Elemental antimony can also be employed.

The amount of antimony compounds as catalysts can be varied within wide limits. A catalytic action is thus already detectable with an addition of 0.0005% by weight. The upper limit of the amount of catalyst is not critical, but high amounts in general offer no advantage in respect of product composition, and often present difficulties during working up. For example, the antimony compound employed as a catalyst is therefore employed in an amount of 0.001 to 0.5% by weight, preferably in an amount of 0.01 to 0.1% by weight. All the amounts are based on the amount of aromatic hydrocarbon employed. It is possible to employ only one antimony compound or several antimony compounds.

The iron compounds are preferably iron halides, in particular iron(III) chloride. Elemental iron can also be employed.

The amount of iron compounds depends on the amount of antimony compounds used. The molar ratio of iron to antimony in the two catalyst components can thus be varied, for example, in the limits from Fe:Sb=2:1 to 1:1000, and this molar ratio is preferably from 1:5 to 1:500. An iron content such as is present, for example, in toluene of industrial quality can therefore be sufficient for the process according to the invention.

Cocatalysts of the formula (II) are employed according to the invention. Preferred compounds of the formula (II) are those in which $R_1$ and $R_2$ in each case independently of one another denote hydrogen, methyl or ethyl or together, with cyclisation, form an ethylene group, $R_3$ denotes hydrogen or methyl and x denotes a number from 1 to 10.

Particular representatives of this embodiment which can be employed are, for example, 12-crown-4 ether, triethylene glycol dimethyl ether, triethylene glycol monomethyl ether or glycol.

The amount of cocatalyst employed depends on the amount of iron catalyst used. The molar ratio of cocatalyst to iron can thus be varied, for example, within the limits of 0.5:1 to 5:1, and this molar ratio is preferably from 1:1 to 2:1.

Any desired sequence of addition of the individual components of the reaction mixture can be chosen. The process according to the invention can be carried out either continuously or discontinuously. Examples of embodiments of the process according to the invention are the following:

A. An aromatic hydrocarbon of the formula (I), for example toluene, is initially introduced into the reaction vessel and brought to the desired temperature (for example 50° C.). The desired amounts of Friedel-Crafts catalyst mixture and cocatalyst are then added in any desired sequence, and gaseous chlorine is passed in, the temperature largely being kept constant, until the desired degree of chlorination is achieved. The mixture is then worked up by distillation.

B. A mixture is prepared from an aromatic hydrocarbon of the formula (I) with a mixture of the Friedel-Crafts catalysts and the cocatalyst, and this is brought to the desired reaction temperature. Chlorinating agent is then added until the desired degree of chlorination is achieved. Here also, working up can be carried out by distillation.

C. A solution of Friedel-Crafts catalyst mixture and cocatalyst in an aromatic hydrocarbon of the formula (I) is prepared and this solution is fed to a continuously operating chlorinating apparatus. The chlorinating agent is likewise passed in continuously at a rate such that the desired degree of chlorination is achieved. Here also, the reaction mixture continuously obtained can be worked up by distillation.

The process according to the invention allows the preparation of nuclear-chlorinated aromatic hydrocarbons with a good stage selectivity, a high content of o-chloro compounds in the reaction mixture and the use of small amounts of catalyst. If solely antimony catalysts are used, according to U.S. Pat. No. 3,226,447, for example, a ratio of o-chlorotoluene to p-chlorotoluene of only 1.6:1 is obtained by chlorination of toluene. If iron is additionally added, the o/p ratio is increased slightly, but at the same time a marked drop in stage selectivity is observed (see Example 5).

EXAMPLES

Unless stated otherwise, percentages are percentages by weight.

EXAMPLE 1

200 g of toluene were weighed at room temperature together with 65 mg of SbCl$_5$, 24 mg of FeCl$_3$ and 26 mg of 12-crown-4 as a cocatalyst (corresponds to a molar ratio of Sb:Fe=1.5:1 and Fe:cocatalyst=1:1) into a blackened chlorinating beaker of 16 cm in height and 6 cm in diameter with 4 baffles. The mixture was then heated to 50° C. under a gentle stream of N$_2$ and introduction of Cl$_2$ directly underneath the stirrer (500 revolutions/minute) was started.

The rate of chlorination was about 20 mol % per hour. After 5 hours, that is to say after introduction of 95 mol % of chlorine, a sample was taken from the reaction mixture and analysed by gas chromatography. The analysis showed the following composition:
toluene 7.4%
o-chlorotoluene 66.5%
m-chlorotoluene 2.2%
p-chlorotoluene 21.9%
dichlorotoluenes 2.0%
o/p ratio=3.04

EXAMPLE 2

The procedure was as in Example 1, but 65 mg of SbCl$_5$, 10 mg of FeCl$_3$ and 11 mg of triethylene glycol dimethyl ether as a cocatalyst (molar ratio of Sb:Fe=7.1:1; molar ratio of Fe:cocatalyst=1:1) were employed. The product composition after 5 hours was:
toluene 5.5%
o-chlorotoluene 67.5%
m-chlorotoluene 2.3%
p-chlorotoluene 21.9%
dichlorotoluenes 2.8% o/p ratio = 3.08

EXAMPLE 3

The procedure was as in Example 1, but 130 mg of SbCl$_5$, 20 mg of FeCl$_3$ and 21 mg of triethylene glycol monomethyl ether as the cocatalyst (molar ratio of Sb:Fe=3.5:1; molar ratio of Fe:cocatalyst=1:1) were employed. The product composition after 5 hours was:
toluene 5.8%
o-chlorotoluene 67.8%
m-chlorotoluene 2.3%
p-chlorotoluene 21.8%
dichlorotoluenes 2.3%
o/p ratio = 3.11

EXAMPLE 4

The procedure was as in Example 1, but 130 mg of SbCl$_5$, 0.5 mg of FeCl$_3$ and 1.0 mg of glycol as the cocatalyst (molar ratio of Sb:Fe=141:1; molar ratio of Fe:cocatalyst=1:5) were employed. The product composition after 5 hours was:
toluene 5.7%
o-chlorotoluene 68.5%
m-chlorotoluene 2.2%
p-chlorotoluene 20.9%
dichlorotoluenes 2.7%
o/p ratio = 3.28

EXAMPLE 5 (for comparison)

The experiment described in Example 2 was carried out without addition of triethylene glycol dimethyl ether. The product composition after 5 hours was:
toluene 8.5%
o-chlorotoluene 56.6%
m-chlorotoluene 2.3%
p-chlorotoluene 25.8%
dichlorotoluenes 6.8%
o/p ratio = 2.19

What is claimed is:

1. A process for the nuclear chlorination of an aromatic hydrocarbon of the formula (I)

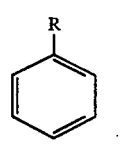
(I)

in which

R denotes a C$_1$–C$_{12}$-alkyl radical or C$_3$–C$_8$-cycloalkyl radical, in the presence of a mixture of Friedel-Crafts catalysts and in the presence of cocatalysts and in the liquid phase, comprising employing a Friedel-Crafts catalyst which is a mixture of at least one antimony compound and at least one iron compound and a cocatalyst which is at least one compound having a polyether structure of the formula (II)

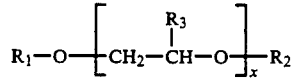
(II)

in which

R$_1$ and R$_2$ independently of one another in each case represent hydrogen, a C$_1$–C$_{18}$-alkyl radical or C$_3$–C$_8$-cycloalkyl radical, or R$_1$ and R$_2$ together represent the radical of a cyclising alkylene group, R$_3$ denotes hydrogen, methyl or ethyl and x denotes a number from 1 to 500.

2. The process of claim 1, in which toluene, ethylbenzene, propylbenzene cumene, tert-butylbenzene or phenylcyclohexane is employed as the aromatic hydrocarbon of the formula (I).

3. The process of claim 1, in which the cocatalyst of the formula (II) is one wherein R$_1$ and R$_2$ in each case independently of one another denote hydrogen, methy or ethy or together, with cyclisation, form an ethylene group.

R$_3$ denotes hydrogen or methyl and x denotes a number from 1 to 10.

4. The process of claim 1, in which the chlorination is carried out using elemental chlorine.

5. The process of claim 1, in which a reaction temperature in the range from 0° to 100° C. is applied.

6. The process of claim 1, in which iron (III) chloride or elemental iron is employed as the iron compound and SbCl$_3$, SbCl$_5$ or elemental antimony is employed as the antimony compound.

7. The process of claim 1, in which the antimony compound is employed in an amount of 0.001 to 0.5% by weight, based on the aromatic hydrocarbon of the formula (I) employed.

8. The process of claim 1, in which the molar ratio of iron to antimony is 2:1 to 1:1000, based on the antimony employed in the antimony compound used.

9. The process of claim 1, in which the cocatalyst is employed in a molar ratio of 0.5:1 to 5:1, based on the iron employed.

* * * * *

UNITED STATES PATENT AND TRADEMARK OFFICE
CERTIFICATE OF CORRECTION

PATENT NO : 5,315,049
DATED    : May 24, 1994
INVENTOR(S): Schrage, et al.

It is certified that error appears in the above-identified patent and that said Letters Patent is hereby corrected as shown below:

Title Page    U.S. PATENT DOCUMENTS: After " 3,000,975, 9/1961 , delete " De Bella " and substitute -- Di Bella --

Col. 6, line 23    After " propylbenzene " insert -- , --

Signed and Sealed this

Fifth Day of October, 1999

Attest:

Q. TODD DICKINSON

Attesting Officer    Acting Commissioner of Patents and Trademarks